United States Patent

Rajasekaran

Patent Number: 5,390,859
Date of Patent: Feb. 21, 1995

[54] LOW PRESSURE, SHEAR-TYPE CELL HOMOGENIZER AND METHOD OF USING

[75] Inventor: Ayyappan K. Rajasekaran, New York, N.Y.

[73] Assignee: Cornell Research Foundation, Inc., Ithaca, N.Y.

[21] Appl. No.: 132,475

[22] Filed: Oct. 6, 1993

[51] Int. Cl.⁶ .................... B09B 3/00; B02C 19/08
[52] U.S. Cl. ........................... 241/2; 241/114; 241/169; 241/169.1; 241/199.12; 241/261.2
[58] Field of Search ............... 241/2, 114, 169, 169.2, 241/169.1, 199, 199.7, 199.8, 199.9, 199.11, 199.12, 261.2, 257.1, 259

[56] References Cited

U.S. PATENT DOCUMENTS

| | | | |
|---|---|---|---|
| 1,924 | 3/1965 | Varney | 241/261.2 X |
| 527,986 | 10/1894 | Howe | 241/14 X |
| 2,606,722 | 8/1952 | Grönberg | 241/261.2 X |
| 2,652,202 | 9/1953 | Mallinson et al. | 241/261.2 |
| 3,556,414 | 1/1971 | Eberly, Jr. | |
| 3,941,317 | 3/1976 | Kanor | |
| 4,307,846 | 12/1981 | Spelsberg | |
| 4,333,611 | 6/1982 | Zucker et al. | |
| 4,350,768 | 9/1982 | Tihon et al. | |
| 4,509,695 | 4/1985 | Bessman | |
| 4,828,395 | 5/1989 | Saito et al. | |
| 5,279,463 | 1/1994 | Holl | 241/261.1 X |

FOREIGN PATENT DOCUMENTS

1620133  1/1991  U.S.S.R. ............. 241/261.2

*Primary Examiner*—Timothy V. Eley
*Attorney, Agent, or Firm*—Perman & Green

[57] ABSTRACT

A method for rupturing cell walls and membranes of organic cells while leaving intra-cellular organelles substantially intact employs a culture dish for holding the cells. A pestle includes a cylindrical portion that metes with the culture dish. Extending from the cylindrical portion is an axially aligned shaft. The method includes the steps of: emplacing a layer of cells in the culture dish; placing the pestle in contact with the layer of cells; applying a pressure axially to the shaft to force the pestle into contact with the cells; and rotating the shaft and pestle a plurality of reverse-direction partial rotations to achieve a rupture of cellular membranes of cells within the culture dish. Both the base of the culture dish and the pestle are substantially planar thereby enabling uniform pressure application across the base of the culture dish.

8 Claims, 1 Drawing Sheet

LOW PRESSURE, SHEAR-TYPE CELL HOMOGENIZER AND METHOD OF USING

FIELD OF THE INVENTION

This invention relates to cell homogenizers, and more particularly, to an apparatus and method for rupturing cell walls and membranes, while leaving internal cell organelles substantially unharmed.

BACKGROUND OF THE INVENTION

Research on sub-cellular components is an increasingly important area of biological investigation. As part of this work, it is necessary to isolate sub-cellular organelles. Isolation includes disruption or breaking apart of cell membranes without damaging the organelles, i.e., cell nuclei, mitochondria, endoplasmic reticulum, Golgi complex, lysosomes, etc. Prior art apparatus has enabled fragments of these organelles to be isolated, however such apparatus, in general, is not able to isolate intact organelles, as observed in-vivo. For example, endoplasmic reticulum occurs as tubular and sheet-like cisternae and golgi complex appear as stacks of cisternae inside the cell. However, after cells are homogenized and fractionated, the aforesaid organelles no longer resemble their previously intact, in-vivo formations. Thus, it has been heretofore difficult to study mechanisms that maintain the structure of such intracellular organelles.

Many prior art homogenizers use cell suspensions obtained either by scraping the cells from a culture dish (where the cells were grown) or by centrifugation when the cells are grown in suspension. Such cells are then re-suspended in a hypotonic buffer solution. This treatment swells the cells, resulting in a weakening of the cell membranes. The membranes are then disrupted in a Dounce homogenizer which includes a glass tube-like receptacle in which the cell suspension is placed and a pestle which can fit either tightly or loosely into the receptacle. By moving the pestle up and down in the glass cylinder, cell disruption is achieved. The cell-rupturing action of a Dounce homogenizer does not result in a breakage of all cells during a single stroke of the pestle. In general, many strokes must be employed to obtain a disrupted cell population (e.g., from 25 to 50 strokes). Because of this extensive homogenization procedure, the delicate intra-cellular membranous organelles are broken and lose their structure.

A further type of homogenizer, that, at times, does enable recovery of some intact Golgi structures is the ball homogenizer developed by Balch and Rothman. The ball homogenizer has a steel ball that moves inside of a cylinder, the movement of the ball modulated by pressure applied on the sides of the cylinder using syringes. The space between the ball and the cylinder varies as a result, and cells are disrupted to a various extent by use of balls of different sizes.

A variety of other types of homogenizers are disclosed in the prior art. In U.S. Pat. No. 3,556,414 to Eberly, Jr., a compression chamber homogenizer is described wherein a mass of animal cells are compacted by a reciprocating plunger rod under pressures of at least 10,000 psi. The cell mass is then disrupted by being discharged into a relatively low pressure environment. Such homogenization action assures both complete disruption of cell membranes, as well as internal organelles. In U.S. Pat. No. 4,333,611 to Zucker et al., a cell mass is initially heated by friction to a temperature above the point of evaporation of water. The cell mass is subsequently expanded into a reduced pressure area so as to enable rupturing of the cell walls.

U.S. Pat. Nos. 3,941,317 to Kanor and 4,350,768 to Tihon et al., both describe apparatus for disaggregating tissue which involve the forcing of a cell mass through a screen-like membrane or structure. By repeated actions of the apparatus, cellular components are "disaggregated".

In U.S. Pat. No. 4,509,695 to Bessman, a tissue pulverizer is described wherein the tissue is initially frozen and then placed between a mortar and pestle that have been cooled with liquid nitrogen. The pestle is then struck with a hammer to pulverize the frozen sample. U.S. Pat. Nos. 4,307,846 to Spelsberg and 4,828,395 to Saito et al., both disclose continuous-flow type tissue homogenizers similar in construction to the Dounce homogenizer described above. In specific, such homogenizers include a generally tubular container with an inner surface defining a tissue homogenization chamber. One end of the container has an inlet for introduction of non-homogenized tissue. A pestle member is disposed within the tubular chamber and is mounted for rotative movement. Grooves about the pestle's outer surface channel force the tissue between the wall of the pestle member and the inner wall of the tubular container where homogenization occurs.

With the sole exception of the Balch and Rothman ball homogenizer, each of the above described homogenizers results not only in disruption of cell membranes but also of internal organelles. Further, the use of hypotonic solutions to assist in the cell disruption process further injures internal organelle structures.

Accordingly, it is an object of this invention to provide a cell homogenizer which leaves substantially intact, intra-cellular organelles.

It is a further object of this invention to provide a cell homogenizer which operates upon cells still attached to a surface of a cell culture dish.

It is yet another object of this invention to provide a cell homogenizer for exposing cellular domains such as apical or basolateral domain of epithelial cells grown attached to a surface of a culture dish.

It is still a further object of this invention to provide a cell homogenizer that is adapted to operate with both plant and mammalian cells.

It is still another object of this invention to provide a cell homogenizer that is adapted to operate with solid tissue and with cells grown in suspension culture.

It is another object of this invention to provide a cell homogenizer which is of inexpensive construction and may be used in the research laboratory.

It is yet another object of this invention to provide an improved cell homogenizer which operates through the application of low pressure to achieve cell wall or membrane breakage.

SUMMARY OF THE INVENTION

A method for rupturing cell walls and membranes of organic cells while leaving intra-cellular organelles substantially intact employs a culture dish for holding the cells. A pestle includes a cylindrical portion that mates with the culture dish. Extending from the cylindrical portion is an axially aligned shaft. The method includes the steps of: emplacing a layer of cells in the culture dish; placing the pestle in contact with the layer of cells; applying a pressure axially to the shaft to force the pestle into contact with the cells; and rotating the shaft and pestle a plurality of reverse-direction partial rotations to achieve a rupture of cellular membranes of cells within the culture dish. Both the base of the culture dish and the pestle are substantially planar thereby enabling uniform pressure application across the base of the culture dish.

DETAILED DESCRIPTION OF THE INVENTION

Figure 1:
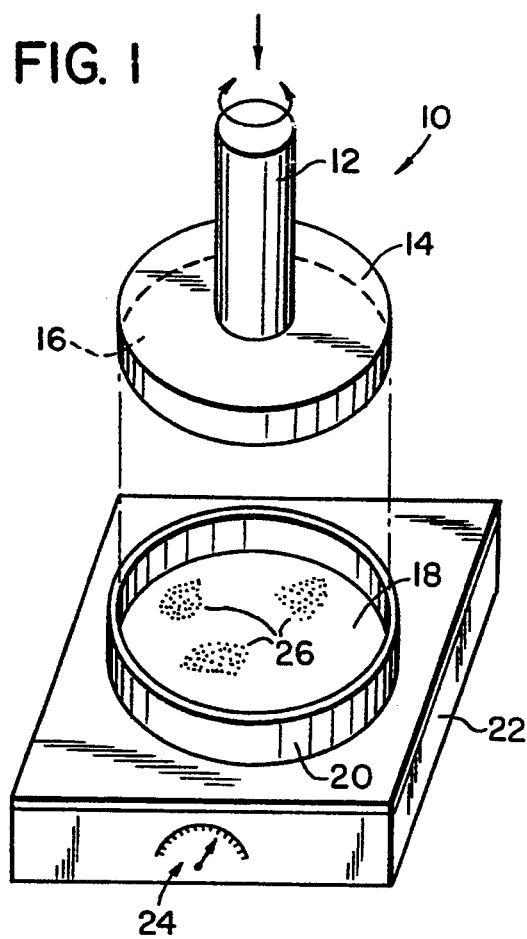
FIG. 1 is a perspective view of a homogenizer that operates in accordance with the method of the invention.

Referring to FIG. 1, a cell homogenizer incorporating the invention includes a pestle 10 that includes a shaft portion 12 and a bearing member 14. Bearing member 14 has a planar lowermost surface 16 which mates with bottom surface 18 of a tissue culture dish 20. Tissue culture dish 20 is supported upon a scale 22 that is calibrated to show (by indicator 24) the amount of axial pressure placed upon culture dish 20.

Cells 26 that are to be homogenized are immersed in an isotonic solution within culture dish 20.

It has been found that application of approximately 3 to 4 lbs. of pressure to shaft 12, while rotating pestle 10 with two to four partial rotations (e.g., approximately 90° each), achieves substantial destruction of the membranes of mammalian cells 26 while leaving intra-cellular organelles substantially undamaged. To increase the frictional shear force exerted by pestle 10 upon cells 26, bearing surface 16 may be slightly roughened (such as by sandblasting). If plant cells are to be homogenized, it has been found that a substantially increased pressure should be applied, i.e. 20 to 30 pounds.

It is important that the pressure be applied along the center-line of shaft 12 so that forces are equally distributed between lowermost surface 16 and bottom surface 18 of culture dish 20. This enables a uniformity of cell homogenization to be achieved.

Experimental Results

A prototype of the homogenizer shown in FIG. 1 was constructed employing acrylic components for pestle 10. A plastic tissue culture dish 20 was employed that had a flat bottom surface 18 of approximately 10 cm². The efficiency of cell breakage was studied by providing a known amount of frictional force to cells 26 (in an isotonic buffer) and by rotation of pestle 10 in a defined manner. The homogenate was then visualized by an inverted phase-contrast microscope to assess the extent of cell breakage.

A 10 cm² tissue culture disk containing a monolayer of MDCK(Madin Darby Canine Kidney) cells was kept on a micro-biological inoculating turntable which aided in giving defined rotations. The pressure given to the cells was monitored by mounting the set-up on a weighing scale. The force on pestle 10 was exerted manually by pressing shaft 12 downwardly. The movements of cell culture dish 20 were achieved by rotating the turntable simultaneously with the application of pressure.

A "shear stroke" is defined as one complete clockwise or anti-clockwise 360° rotation of pestle 10 with respect to cell culture dish 20. The time duration of a shear stroke varied from 5–20 seconds, depending on the given pressure. Two different types of shear strokes were used: complete shear strokes of 360° and partial shear strokes (approximately 90°) taking less than 2 seconds per partial shear stroke.

The criteria for proper cell homogenization was assessed by intactness of all nuclei as observed by inverted phase contrast microscopy. The cell monolayer was washed once in a phosphate buffer saline isotonic solution and 400 or 800 microliters of the same buffer were used for homogenization. Initially, 25–30 lbs. of pressure were applied with 8 shear strokes and the homogenate was visualized. The cells were completely destroyed and the nuclei were broken into pieces showing that the applied pressure was too large. When 6–8 lbs. of pressure was applied with three shear strokes, again all cells were broken, including the nuclei. When 3–4 lbs. of pressure was applied with 3 complete shear strokes, both cell and nuclei destruction were again observed. When 3–4 lbs. was applied with 2 rapid partial strokes (90° each) the cell walls were observed as broken and the nuclei were seen as being intact. By contrast, using a Dounce homogenizer and an isotonic buffer cell solution, 15 strokes (with one stroke being one complete upward and downward movement of the pestle) resulted in most of the cells being unbroken.

Figure 2:
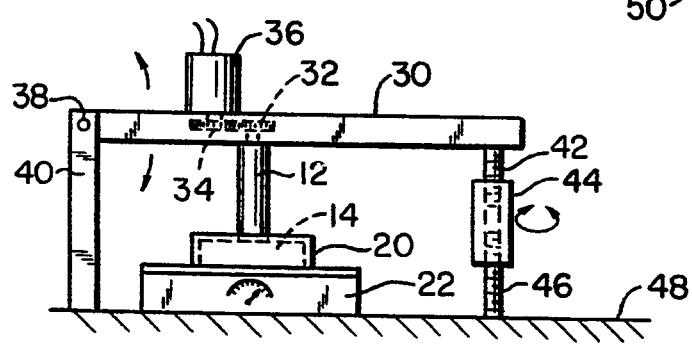
FIG. 2 is a side view of an apparatus for controlling both the pressure exerted upon the pestle and for causing desired rotations thereof.

Referring to FIG. 2, a mechanism is shown for controlling the amount of pressure applied to pestle 10 and for simultaneously causing clockwise and counter clockwise rotation of shaft 12. A lever arm 40 includes a female opening 32 that accepts the topmost portion of shaft 12. In this case, the topmost portion of shaft 12 is provided with gear teeth that mate with a gear 34 that is, in turn, connected to a reversible motor 36. Arm 30 is pivotable about pivot point 38 which is, in turn, attached to a vertical support 40.

At one end of arm 30, a threaded rod 42 extends downwardly and is engaged by a threaded sleeve 44. An oppositely disposed threaded rod 46 extends upwardly from surface 48 and is engaged by threaded sleeve 44. Rods 42 and 46 are oppositely threaded so that rotation of sleeve 44 causes them to either move together or apart, as the case may be. Thus to properly adjust the pressure between bearing member 14 and culture dish 20, sleeve 44 is rotated until scale 22 indicates the proper pressure. At this point, the scale surface is locked.

A user initially places the cells to be homogenized in culture dish 20 and places pestle 10 therein. The geared upper portion (not shown) of shaft 12 is then fitted into opening 32 so that it engages gear 34. The user then adjusts the pressure applied to arm 30 to achieve the desired pestle/cell pressure (as indicated by scale 22), locks the scale and sequences motor 36 through plural partial shear strokes by an appropriate control circuit (not shown).

Figure 3:
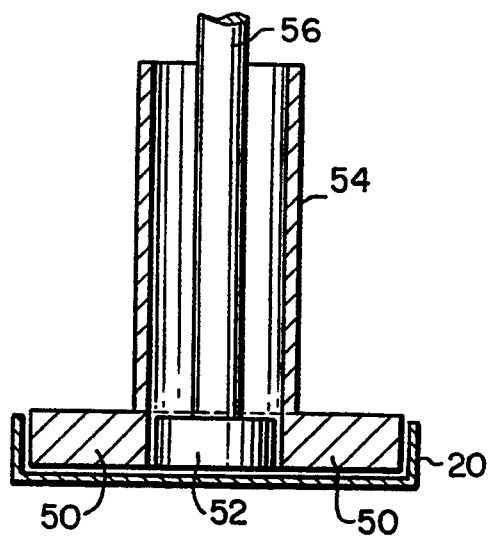
FIG. 3 is a side, partial sectional view of a further embodiment of the invention.

In FIG. 3, a further embodiment is shown of the invention. The homogenizer of FIG. 3 comprises two pestles 50 and 52, both provided with a flat bottoms. Pestle 52 nests within a hollow shaft 54 that is attached to pestle 50. A further shaft 56 is attached to pestle 52. The design of the homogenizer shown in FIG. 3 overcomes a potential problem with the homogenizer of FIG. 1. In particular, the homogenizer of FIG. 1 subjects cells about the periphery of cell culture dish 20 to a greater length of shear stroke than those cells that are nearer the center of culture dish 20. The arrangement of pestles shown in FIG. 3 enables approximately equal amounts of shear strokes to be applied to cells about the periphery of culture dish 20 (beneath pestle 50) and to those cells beneath pestle 52. Thus, the amounts of clockwise and counter-clockwise rotation of pestles 52 and 50 are adjusted such that each provides an approximately equal amount of shear stroke to cells that reside beneath the bottom surfaces of pestles 50 and 52.

In summary, a method and apparatus is shown for enabling homogenization of cellular structures without substantial injury to intra-cellular organelles. For mammalian cells the applied relative pressure between the pestle and cell dish should not exceed 5 to 10 lbs. and the number of partial shear strokes should not exceed 5. It is preferred that a pressure of 3 to 4 lbs. be applied, with three counter-rotating partial shear strokes. For plant cells, the applied pressure should preferably be in the range of 20–30 lbs., with sufficient counter-rotating shear strokes applied to rupture the cell membranes. However, it will be understood by those skilled in the art that there is an empirical relationship between the number of shear strokes (or partial shear strokes) and applied pressure. In essence, the greater the pressure, the less the number of shear strokes and their angular application.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for homogenizing cells while leaving substantially intact, intracellular organelles, the method employing a flat-bottom dish for holding the cells, a pestle having a planar bearing member that intimately mates with said flat-bottom dish, the method comprising the steps of:

emplacing said cells and an isotonic solution in said dish;

placing said bearing member of said pestle in contact with said cells;

applying pressure between said bearing member and said dish, said pressure substantially evenly distributed over mating surfaces of said bearing member and said dish, and causing relative rotative movement between said bearing member and said dish, said relative rotative movement comprising plural successive clockwise and counterclockwise rotations.

2. The method as recited in claim 1 wherein said pressure does not exceed ten pounds and each rotation does not exceed 180°.

3. The method as recited in claim 1 wherein said relative pressure is within the range of two to four pounds.

4. The method as recited in claim 1 wherein each rotation is approximately 90° and a total number of said successive rotations does not exceed 4.

5. Apparatus for homogenizing cells while leaving intra-cellular organelles substantially intact, said apparatus comprising:

a cell dish having a recessed, continuous planar bottom surface for receiving and holding cells to be homogenized;

a pestle having a single planar bearing member that intimately mates with said recessed planar bottom surface of said cell dish; and means for applying a relative pressure between said single planar bearing member and said recessed planar bottom surface so that said relative pressure is substantially evenly distributed across mating surfaces therebetween and is of a magnitude to rupture cell walls while leaving intra cellular organelles intact, and for further causing plural relative counter-rotations between said recessed planar bottom surface and said single planar bearing member.

6. The apparatus as recited in claim 5 wherein said single planar bearing member is roughened.

7. Apparatus for homogenizing cells while leaving intra-cellular organelles substantially intact, said apparatus comprising:

a cell dish having a planar bottom surface for receiving cells to be homogenized;

a first pestle having a planar bearing surface that mates with said planar bottom surface of said cell dish, said first pestle having a central orifice;

a second pestle having a planar bearing surface that mates with said planar surface of said cell dish, fitted within said second orifice, said first and second pestles independently movable with respect to each other; and means for applying a relative pressure between said pestles and said planar bottom surface that is substantially evenly distributed across said planar bottom surface and for causing relative rotations between said pestles and said planar bottom surface.

8. The apparatus as recited in claim 7 wherein said planar bearing surfaces are roughened.

* * * * *